United States Patent [19]

Algieri et al.

[11] Patent Number: 4,788,184

[45] Date of Patent: Nov. 29, 1988

[54] SUBSTITUTED 3-CYCLOBUTENE-1,2-DIONES AS ANTI-ULCER AGENTS

[75] Inventors: Aldo A. Algieri, Fayetteville; Ronnie R. Crenshaw, Dewitt, both of N.Y.

[73] Assignee: Bristol-Myers Company, New York, N.Y.

[21] Appl. No.: 132,615

[22] Filed: Nov. 13, 1987

Related U.S. Application Data

[60] Continuation of Ser. No. 926,874, Nov. 6, 1986, abandoned, which is a continuation of Ser. No. 656,203, Oct. 1, 1984, abandoned, which is a division of Ser. No. 503,996, Jun. 13, 1983, Pat. No. 4,503,051, which is a division of Ser. No. 369,971, Apr. 21, 1982, Pat. No. 4,522,943, which is a continuation-in-part of Ser. No. 264,533, May 18, 1981, Pat. No. 4,390,701.

[51] Int. Cl.⁴ .................... A61K 31/55; A61K 31/38; C07D 409/06; C07D 409/14
[52] U.S. Cl. .................... 514/183; 514/216; 514/222; 514/230; 514/252; 514/253; 514/318; 514/321; 514/326; 514/333; 514/336; 514/338; 514/343; 514/422; 514/427; 514/438; 514/444; 514/445; 540/480; 540/582; 540/596; 540/597; 544/58.6; 544/58.7; 544/131; 544/146; 544/360; 544/364; 544/377; 544/379; 546/194; 546/197; 546/213; 546/256; 546/270; 546/281; 546/284; 548/526; 548/527; 549/65; 549/77
[58] Field of Search .................... 549/77, 65; 544/58.6, 544/58.7, 131, 146, 360, 364, 377, 379; 546/194, 197, 213, 256, 270, 281, 284; 548/526, 527; 514/216, 222, 230, 252, 253, 318, 321, 326, 333, 336, 343, 422, 438, 444, 445, 183, 338, 427; 540/480, 596, 582, 597

[56] References Cited

U.S. PATENT DOCUMENTS

| 4,062,863 | 12/1977 | Ganellin et al. | 548/342 X |
|---|---|---|---|
| 4,239,769 | 12/1980 | Price et al. | 549/65 |
| 4,390,701 | 6/1983 | Algieri et al. | 546/235 |
| 4,395,553 | 7/1983 | Algieri et al. | 546/235 |
| 4,503,051 | 3/1985 | Algieri et al. | 514/183 |
| 4,522,943 | 6/1985 | Algieri et al. | 514/183 |
| 4,526,973 | 7/1985 | Algieri et al. | 546/235 |
| 4,539,316 | 9/1985 | Algieri et al. | 514/212 |
| 4,546,188 | 10/1985 | Algieri et al. | 546/194 |
| 4,607,105 | 8/1986 | Algieri et al. | 546/213 |

FOREIGN PATENT DOCUMENTS 10418 4/1980 European Pat. Off. ............ 564/346

OTHER PUBLICATIONS

Brittain, R. et al., *Tips*, Nov. 1981, pp. 310-313.

*Primary Examiner*—Richard A. Schwartz
*Attorney, Agent, or Firm*—Aldo A. Algieri

[57] ABSTRACT

Compounds of the formula

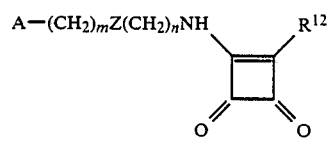

wherein $R^{12}$ is a leaving group, Z is S, O or $CH_2$ and A is a phenyl, furyl, thienyl or pyridyl ring substituted by a

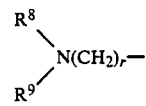

moiety, in which $R^8$ and $R^9$ are various substituents or, when taken together with the nitrogen, may be a specified heterocyclic ring, are intermediates in the preparation of histamine $H_2$-antagonist anti-ulcer agents of the formula

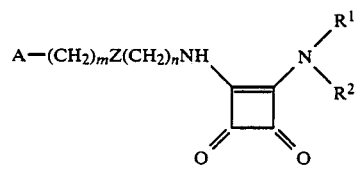

in which $R^1$ and $R^2$ are any of several specified substituents.

10 Claims, No Drawings

SUBSTITUTED 3-CYCLOBUTENE-1,2-DIONES AS ANTI-ULCER AGENTS

CROSS-REFERENCE TO RELATED APPLICATIONS

This application is a continuation of application Ser. No. 926,874 filed 11/6/87, now abandoned, which is a continuation of application Ser. No. 656,203 filed Oct. 1, 1984, now abandoned, which is a divisional of our prior co-pending application Ser. No. 503,996, filed June 13, 1983, now U.S. Pat. No. 4,503,051, which is a divisional of our prior co-pending application Ser. No. 369,971, filed Apr. 21, 1982, now U.S. Pat. No. 4,522,943 which is a continuation-in-part of our prior, co-pending application Ser. No. 264,533, filed May 18, 1981, now U.S. Pat. No. 4,390,701.

SUMMARY OF THE INVENTION

Certain substituted 1,2-diaminocyclobutene-3,4-diones of the formula

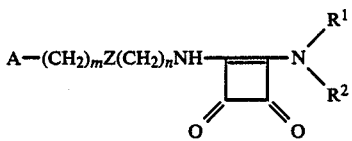

wherein A is substituted phenyl, furyl, thienyl or pyridyl, Z is sulfur, oxygen or methylene, m is 0-2, n is 2-5 and $R^1$ and $R^2$ are as defined below, are potent histamine $H_2$-antagonists, inhibit gastric acid secretion and are useful in the treatment of peptic ulcers.

BACKGROUND AND PRIOR ART

Burimamide (IIa) was the first clinically effective $H_2$-receptor antagonist. It inhibits gastric secretion in animals, including man, but oral absorption is poor.

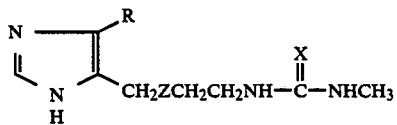

| | | |
|---|---|---|
| IIa; R = H, Z = $CH_2$, X = S | Burimamide |
| b; R = $CH_3$, Z = S, X = S | Metiamide |
| c; R = $CH_3$, Z = S, X = NCN | Cimetidine |

Metiamide (IIb), a subsequently evaluated $H_2$-antagonist, is more potent than burimamide and is orally active in man. Clinical utility was limited, however, owing to toxicity (agranulocytosis). Cimetidine (IIc) is as effective an $H_2$-antagonist as metiamide, without producing agranulocytosis, and has recently been marketed as an anti-ulcer drug.

Reviews on the development of $H_2$-antagonists, including those discussed in the preceding paragraph, may be found in C. R. Ganellin, et al., *Federation Proceedings*, 35, 1924 (1976), in *Drugs of the Future*, 1, 13 (1976) and in references cited therein.

U.S. Pat. No. 4,062,863 discloses histamine $H_2$-antagonists of the formula

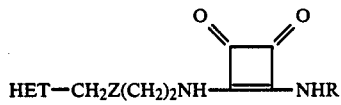

wherein R is hydrogen, (lower)alkyl or $(CH_2)_2Z'CH_2$—HET'; Z and Z' each are sulfur or methylene; and HET and HET' each are an imidazole ring optionally substituted by methyl or bromo, a pyridine ring optionally substituted by hydroxy, methoxy, chloro or bromo, a thiazole ring or an isothiazole ring, and pharmaceutically acceptable acid addition salts thereof. U.S. Pat. Nos. 4,120,968, 4,120,973 and 4,166,857 are divisionals thereof which have substantially the same disclosure.

U.K. published patent application No. 2,023,133 discloses histamine $H_2$-antagonists of the formula

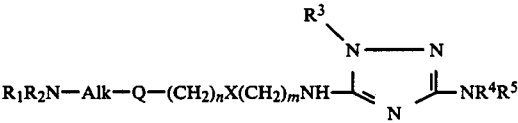

wherein $R_1$ and $R_2$ are independently hydrogen, alkyl, cycloalkyl, alkenyl, alkynyl, aralkyl, trifluoroalkyl or alkyl substituted by hydroxy, alkoxy, amino, alkylamino, dialkylamino or cycloalkyl, or $R_1$ and $R_2$, taken together with the nitrogen to which they are attached, may be a 5- to 10-membered alicyclic heterocyclic ring which may be saturated or may contain at least one double bond, which may be substituted by one or more alkyl groups or a hydroxy group and/or which may contain another heteroatom; Alk is a straight or branched alkylene chain of 1-6 carbon atoms; Q is a furan or thiophene ring incorporated into the molecule via the 2- and 5-positions, the furan ring optionally bearing a further substituent $R_7$ adjacent the $R_1R_2N$—Alk-group, or Q is a benzene ring incorporated into the molecule via its 1- and 3- or 1- and 4-positions; $R_7$ is halogen, alkyl (which may be substituted by hydroxy or alkoxy); X is methylene, oxygen, sulfur or

in which $R^6$ is hydrogen or methyl; n is 0, 1 or 2; m is 2, 3 or 4; $R_3$ is hydrogen, alkyl, alkenyl, aralkyl, hydroxyalkyl having at least two carbon atoms, alkoxyalkyl or aryl; and $R_4$ and $R^5$ are independently hydrogen, alkyl, alkyl substituted by hydroxy or $C_{1-3}$ alkoxy, alkenyl, aralkyl or heteroaralkyl, or $R_4$ and $R_5$ taken together with the nitrogen to which they are attached, may be a 5- to 7-membered saturated heterocyclic ring which may contain another heteroatom or the group

or $R_4$ and $R_5$ taken together may be the group

wherein $R_8$ is aryl or heteroaryl and $R_9$ is hydrogen or alkyl; and physiologically acceptable salts and hydrates thereof.

Published European patent application No. 30,092 discloses histamine $H_2$-antagonists of the formula

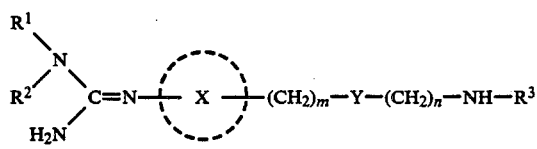

in which $R^1$ and $R^2$ are hydrogen or optionally halogen-substituted alkyl, cycloalkyl or cycloalkylalkyl, provided that at least one of $R^1$ and $R^2$ is halogen-substituted alkyl, cycloalkyl or cycloalkylalkyl;

X is a phenyl ring with 1 or 2 optional substituents or a 5- or 6-membered heterocyclic aromatic ring containing 1, 2 or 3 heteroatoms selected from O, N and S, the heterocyclic ring, where possible, having 1 optional substituent, which optional substituents are halogen, alkyl, alkoxy, alkylthio, trifluoromethyl, hydroxy and amino;

Y is O, S, a direct bond, methylene, cis or trans vinylene, sulfinyl or $NR^4$ in which $R^4$ is H or alkyl;

m is 0 to 4 and n is 1 to 5;

$R^3$ is inter alia AB in which A is inter alia a 3,4-dioxocyclobuten-1,2-diyl radical and B is inter alia the radical $NR^7R^8$ in which $R^7$ and $R^8$ are inter alia hydrogen, alkyl, haloalkyl, alkoxycarbonyl, alkenyl, alkynyl, (primary hydroxy)alkyl or (primary amino)alkyl, or $R^8$ and $R^9$, together with the nitrogen atom to which they are attached, may be a 5- to 6-membered ring which optionally contains O or $NR^9$ in which $R^9$ is H or alkyl.

Complete Disclosure

This application relates to histamine $H_2$-antagonists which are effective inhibitors of gastric acid secretion in animals, including man, which are useful in the treatment of peptic ulcers and other conditions caused or exacerbated by gastric acidity, and which have the formula

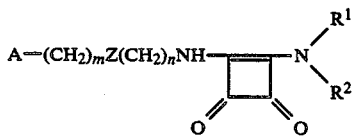

wherein $R^1$ and $R^2$ each are independently hydrogen or (lower)alkyl, and, when $R^1$ is hydrogen, $R^2$ also may be allyl, propargyl, cyclo(lower)alkyl(lower)alkyl, cyclo(lower)alkyl, cyano(lower)alkyl, 2-fluoroethyl, 2,2,2-trifluoroethyl, hydroxy, 2,3-dihydroxypropyl,

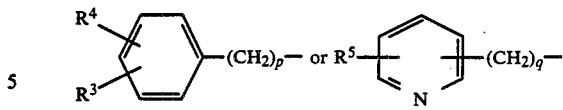

in which p is an integer of from 1 to 6 inclusive,
q is an integer of from 1 to 6 inclusive,
$R^3$ and $R^4$ each are independently hydrogen, (lower)alkyl, hydroxy, (lower)alkoxy or halogen, and, when $R^3$ is hydrogen, $R^4$ also may be trifluoromethyl, or $R^3$ and $R^4$, taken together, may be methylenedioxy,
$R^5$ is hydrogen, (lower)alkyl, (lower)alkoxy, hydroxy, amino or halogen;
m is an integer of from 0 to 2 inclusive;
n is an integer of from 2 to 5 inclusive;
Z is sulfur, oxygen or methylene; and
A is

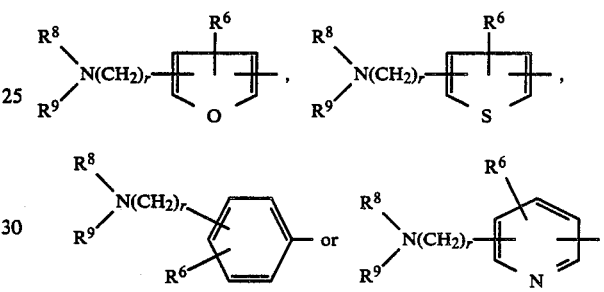

in which $R^6$ is hydrogen, (lower)alkyl, (lower)alkoxy or halogen;

r is an integer of from 1 to 4 inclusive; and $R^8$ and $R^9$ each are independently hydrogen, (lower)alkyl, allyl, propargyl, (lower)alkoxy(lower)alkyl in which the (lower)alkoxy moiety is at least two carbon atoms removed from the nitrogen atom, cyclo(lower)alkyl, or phenyl(lower)alkyl, provided that $R^8$ and $R^9$ may not both be cyclo(lower)alkyl, or $R^8$ and $R^9$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, 1,2,3,6-tetrahydropyridyl, 3-pyrrolino, homopiperidino, heptamethyleneimino, octamethyleneimino or 3-azabicyclo[3.2.2]nonane;

or a nontoxic, pharmaceutically acceptable salt, hydrate or solvate thereof.

This application also relates to processes for the preparation of the compounds of Formula I and to intermediates in the preparation of the compounds of Formula I.

The present invention includes within its scope all possible tautomeric forms, geometric isomers, optical isomers and zwitterionic forms of the compounds of Formula I, as well as mixtures thereof. As used herein and in the claims, the terms "(lower)alkyl" and "(lower)alkoxy" mean straight or branched chain alkyl or alkoxy groups containing from 1 to 6 carbon atoms. Preferably these groups contain from 1 to 4 carbon atoms and, most preferably, they contain 1 or 2 carbon atoms. The term "cyclo(lower)alkyl", as used herein and in the claims, means a cycloalkyl ring containing from 3 to 7 carbon atoms and preferably from 3 to 6 atoms. Unless otherwise specified in the particular instance, the term "halogen" as used herein and in the claims is intended to include chloride, fluorine, bromine and iodine. The term "nontoxic pharmaceutically acceptable salts" is intended to include salts of the compounds of Formula I with any nontoxic pharmaceutically acceptable acid. Such acids are well-known and include hydrochloric, hydrobromic, sulfuric, sulfamic, phosphoric, nitric, maleic, fumaric, succinic, oxalic, benzoic, methanesulfonic, tartaric, citric, camphorsulfonic, levulinic and the like. The salts are made by methods known in the art.

The compounds of Formula I may be prepared by various alternative procedures, utilizing as a starting material a compound of the formula

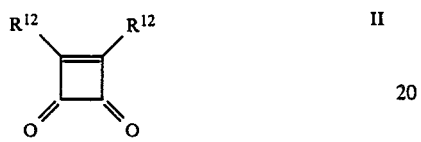

II in which $R^{12}$ is a good leaving group such as halogen, phenoxy, substituted phenoxy, alkoxy or the like. Suitable leaving groups are well-known to those skilled in the art. Preferably, $R^{12}$ is (lower)alkoxy, and especially methoxy and ethoxy.

The compounds of Formula I may be prepared from a compound of Formula II by various alternative reaction schemes. Some of the intermediate compounds are themselves novel.

Reaction Scheme 2

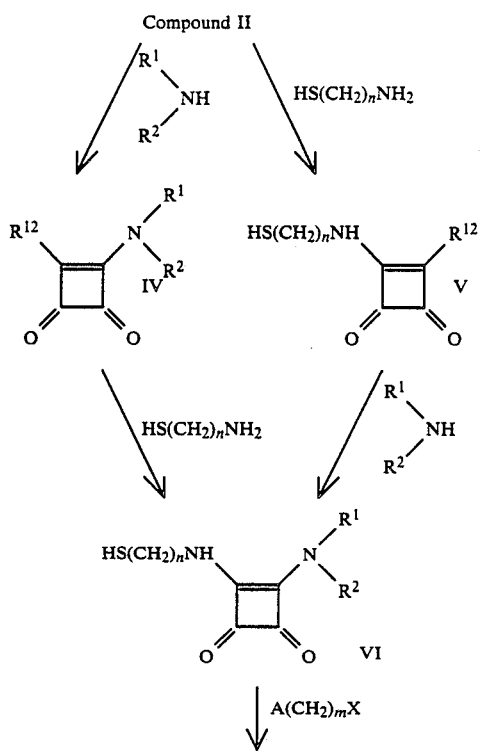

Reaction Scheme 1

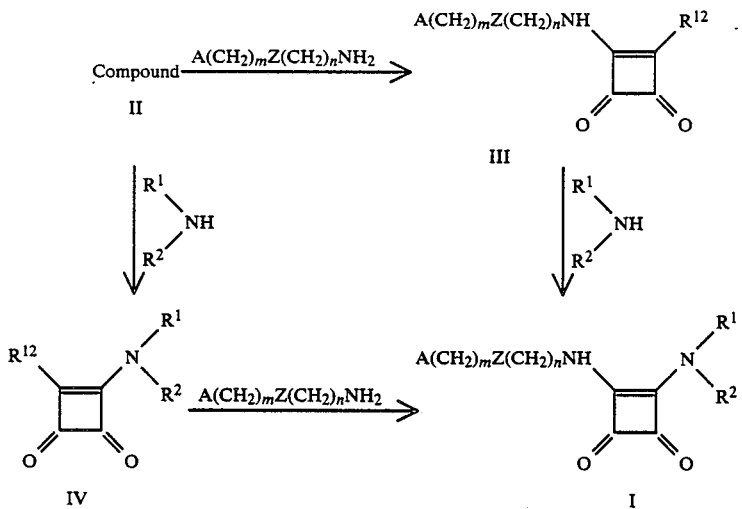

The reactions are conducted in an inert organic solvent; we find methanol to be a convenient and readily available solvent. The reaction temperature is not critical. Most starting materials are quite reactive and we prefer to conduct the reaction at a temperature below room temperature, e.g. 0°–10° C. With some less reactive compounds it is convenient to conduct the reaction at room temperature. Sometimes it is desirable to subsequently raise the temperature of the reaction mixture (e.g. to 50°–60° C.) to complete the reaction.

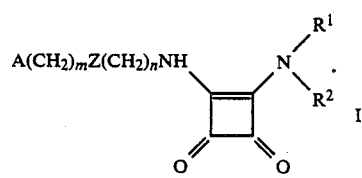

In Reaction Scheme 2, X is a conventional leaving group such as fluoro, chloro, bromo, iodo, $-O_3SR^{13}$ in which $R^{13}$ is (lower)alkyl [e.g. methanesulfonate], aryl or substituted aryl [e.g. benzenesulfonate, p-bromobenzenesulfonate or p-toluenesulfonate], $-O_3SF$, acetoxy or 2,4-dinitrophenoxy. For convenience and economy we prefer to utilize a compound in which X is chloro. The reaction conditions for the preparation of the compounds of Formula IV, V and VI are as described for Reaction Scheme I. The reaction of the compound of Formula VI with $A(CH_2)_mX$ may be conducted in any inert organic solvent such as an alkanol, acetonitrile, dimethylformamide, dimethylsulfoxide, acetone or the like. We prefer to conduct the reaction is an alkanol such as methanol, ethanol or isopropanol. The reaction temperature is not critical; the reaction may be conducted at temperatures of from about 0° to about 200° C. At low temperatures the reaction is slow, while high temperatures normally lead to less pure products due to decomposition and the formation of side-products. We normally prefer to conduct the reaction at room temperature. The reaction of the compound of Formula VI with $A(CH_2)_mX$ to produce the compound of Formula I preferably is conducted in the presence of a base, which facilitates the reaction by acting as an acid acceptor. Suitable bases include, for example, NaOH, KOH, LiOH, triethylamine, dimethylaniline, sodium ethoxide and the like.

In a preferred embodiment of the invention the compounds of Formula I have the structure

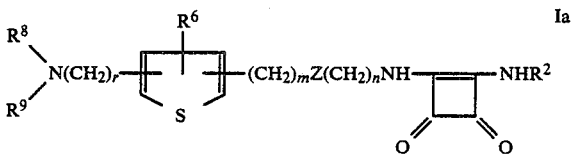

Ia wherein $R^2$ is hydrogen, (lower)alkyl, allyl, propargyl, 3-pyridylmethyl or 6-methyl-3-pyridylmethyl;

m is an integer of from 0 to 2 inclusive;

n is an integer of from 2 to 5 inclusive;

Z is sulfur, oxygen or methylene;

$R^6$ is hydrogen or (lower)alkyl;

r is an integer of from 1 to 4 inclusive; and $R^8$ and $R^9$ each are independently hydrogen or (lower)alkyl, or $R^8$ and $R^9$, taken together with the nitrogen atom to which they are attached, may be pyrrolidino, methylpyrrolidino, morpholino, thiomorpholino, piperidino, methylpiperidino, N-methylpiperazino, 1,2,3,6-tetrahydropyridyl, homopiperidino, heptamethyleneimino, octamethyleneimino or 3-azabicyclo[3.2.2]nonane;

or a nontoxic, pharmaceutically acceptable salt, hydrate or solvate thereof.

In another preferred embodiment of the invention, the compounds of Formula I have the structure

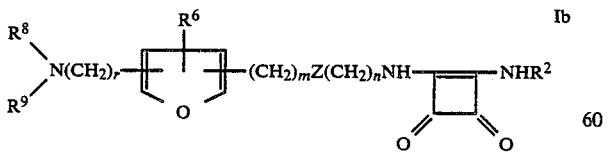

Ib wherein $R^2$ is hydrogen, (lower)alkyl, allyl, propargyl, 3-pyridylmethyl or 6-methyl-3-pyridylmethyl;

m is an integer of from 0 to 2 inclusive;

n is an integer of from 2 to 5 inclusive;

Z is sulfur, oxygen or methylene;

$R^6$ is hydrogen or (lower)alkyl;

r is an integer of from 1 to 4 inclusive; and $R^8$ and $R^9$ each are independently hydrogen or (lower)alkyl, or $R^8$ and $R^9$, taken together with the nitrogen atom to which they are attached, may be pyrrolidino, methylpyrrolidino, morpholino, thiomorpholino, piperidino, methylpiperidino, N-methylpiperazino, 1,2,3,6-tetrahydropyridyl, homopiperidino, heptamethyleneimino, octamethyleneimino or 3-azabicyclo[3.2.2]nonane;

or a nontoxic, pharmaceutically acceptable salt, hydrate or solvate thereof.

In another preferred embodiment of the invention, the compounds of Formula I have the structure

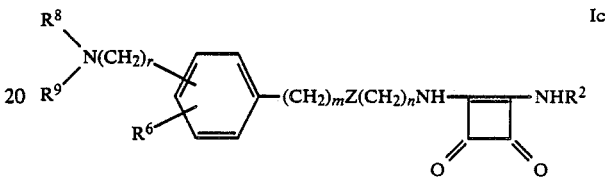

Ic wherein $R^2$ is hydrogen or (lower)alkyl, allyl, propargyl, 3-pyridylmethyl or 6-methyl-3-pyridylmethyl;

m is an integer of from 0 to 2 inclusive;

n is an integer of from 2 to 5 inclusive;

Z is sulfur, oxygen or methylene;

$R^6$ is hydrogen or (lower)alkyl;

r is an integer of from 1 to 4 inclusive; and $R^8$ and $R^9$ each are independently hydrogen or (lower)alkyl, or $R^8$ and $R^9$, taken together with the nitrogen atom to which they are attached, may be pyrrolidino, methylpyrrolidino, morpholino, thiomorpholino, piperidino, methylpiperidino, N-methylpiperazino, 1,2,3,6-tetrahydropyridyl, homopiperidino, heptamethyleneimino, octamethyleneimino or 3-azabicyclo[3.2.2]nonane;

or a nontoxic, pharmaceutically acceptable salt, hydrate or solvate thereof.

In another preferred embodiment of the invention, the compounds of Formula I have the structure

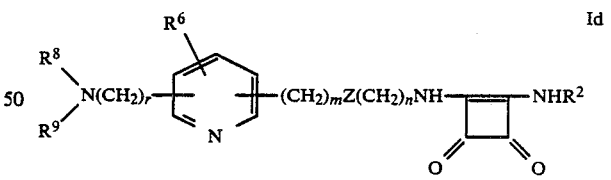

Id wherein $R^2$ is hydrogen or (lower)alkyl, allyl, propargyl, 3-pyridylmethyl or 6-methyl-3-pyridylmethyl;

m is an integer of from 0 to 2 inclusive;

n is an integer of from 2 to 5 inclusive;

Z is sulfur, oxygen or methylene;

$R^6$ is hydrogen or (lower)alkyl;

r is an integer of from 1 to 4 inclusive; and $R^8$ and $R^9$ each are independently hydrogen or (lower)alkyl, or $R^8$ and $R^9$, taken together with the nitrogen atom to which they are attached, may be pyrrolidino, methylpyrrolidino, morpholino, thiomorpholino, piperidino, methylpiperidino, N-methylpiperazino, 1,2,3,6-tetrahydropyridyl, homopiperidino, heptamethyleneimino, octamethyleneimino or 3-azabicyclo[3.2.2]nonane;

or a nontoxic, pharmaceutically acceptable salt, hydrate or solvate thereof.

As presently envisaged, the particularly preferred compounds of Formula I are (a) 1-Amino-2-[3-(3-piperidinomethylphenoxy)propylamino]cyclobutene-3,4-dione, or a nontoxic pharmaceutically acceptable salt, hydrate or solvate thereof.

(b) 1-Amino-2-[3-(3-piperidinomethylphenoxy)propylamino]cyclobutene-3,4-dione hydrochloride.

(c) 1-Amino-2-{2-[(5-dimethylaminomethyl-2-furyl)methylthio]ethylamino}cyclobutene-3,4-dione, or a nontoxic pharmaceutically acceptable salt, hydrate or solvate thereof.

(d) 1-Amino-2-{2-[(5-dimethylaminomethyl-3-thienyl)methylthio]ethylamino}cyclobutene-3,4-dione, or a nontoxic pharmaceutically acceptable salt, hydrate or solvate thereof.

(e) 1-Amino-2-{2-[(5-piperidinomethyl-3-thienyl)methylthio]ethylamino}cyclobutene-3,4-dione, or a nontoxic pharmaceutically acceptable salt, hydrate or solvate thereof.

(f) 1-Amino-2-[3-(3-dimethylaminomethylphenoxy)propylamino]cyclobutene-3,4-dione, or a nontoxic pharmaceutically acceptable salt, hydrate or solvate thereof.

(g) 1-Amino-2-[3-(3-pyrrolidinomethylphenoxy)propylamino]cyclobutene-3,4-dione, or a nontoxic pharmaceutically acceptable salt, hydrate or solvate thereof.

(h) 1-Amino-2-{3-[3-(3-methylpyrrolidino)methylphenoxy]propylamino}cyclobutene-3,4-dione, or a nontoxic pharmaceutically acceptable salt, hydrate or solvate thereof.

(i) 1-Methylamino-2-[3-(3-piperidinomethylphenoxy)propylamino]cyclobutene-3,4-dione, or a nontoxic pharmaceutically acceptable salt, hydrate or solvate thereof.

(j) 2-[3-(3-Piperidinomethylphenoxy)propylamino]-1-(2-propynylamino)cyclobutene-3,4-dione, or a nontoxic pharmaceutically acceptable salt, hydrate or solvate thereof.

(k) 2-[3-(3-Piperidinomethylphenoxy)propylamino]-1-(3-pyridyl)methylaminocyclobutene-3,4-dione, or a nontoxic pharmaceutically acceptable salt, hydrate or solvate thereof.

(l) 1-Amino-2-[3-(3-hexamethyleneiminomethylphenoxy)propylamino]cyclobutene-3,4-dione, or a nontoxic pharmaceutically acceptable salt, hydrate or solvate thereof.

(m) 1-Amino-2-[3-(3-piperidinomethylthiophenoxy)propylamino]cyclobutene-3,4-dione, or a nontoxic pharmaceutically acceptable salt, hydrate or solvate thereof.

(n) 1-Amino-2-[3-(3-heptamethyleneiminomethylphenoxy)propylamino]cyclobutene-3,4-dione, or a nontoxic pharmaceutically acceptable salt, hydrate or solvate thereof.

(o) 1-Amino-2-[3-(3-octamethyleneiminomethylphenoxy)propylamino]cyclobutene-3,4-dione, or a nontoxic pharmaceutically acceptable salt, hydrate or solvate thereof.

In another aspect, this invention relates to novel intermediates of the formula

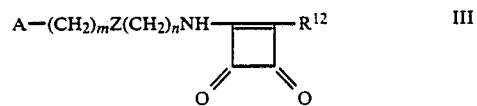

wherein $R^{12}$ is a conventional leaving group selected from halogen, phenoxy, substituted phenoxy and alkoxy;

m is an integer of from 0 to 2 inclusive;

n is an integer of from 2 to 5 inclusive;

Z is sulfur, oxygen or methylene; and

A is

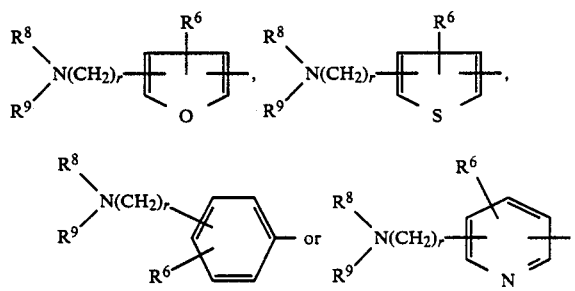

in which $R^6$ is hydrogen, (lower)alkyl, (lower)alkoxy or halogen;

r is an integer of from 1 to 4 inclusive; and $R^8$ and $R^9$ each are independently hydrogen, (lower)alkyl, allyl, propargyl, (lower)alkoxy(lower)alkyl in which the (lower)alkoxy moiety is at least two carbon atoms removed from the nitrogen atom, cyclo(lower)alkyl, or phenyl(lower)alkyl, provided that $R^8$ and $R^9$ may not both be cyclo(lower)alkyl, or $R^8$ and $R^9$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, 1,2,3,6-tetrahydropyridyl, 3-pyrrolino, homopiperidino, heptamethyleneimino, octamethyleneimino or 3-azabicyclo[3.2.2]nonane.

A preferred embodiment of the intermediates of Formula III are those having the structure

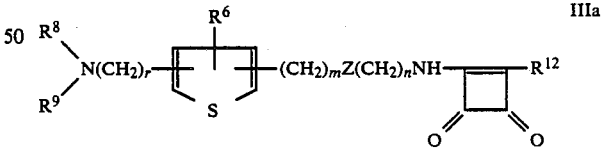

wherein $R^{12}$ is a conventional leaving group selected from halogen, phenoxy, substituted phenoxy and (lower)alkoxy;

m is an integer of from 0 to 2 inclusive;

n is an integer of from 2 to 5 inclusive;

Z is sulfur, oxygen or methylene;

$R^6$ is hydrogen or (lower)alkyl;

r is an integer of from 1 to 4 inclusive; and $R^8$ and $R^9$ each are independently hydrogen or (lower)alkyl, or $R^8$ and $R^9$, taken together with the nitrogen atom to which they are attached, may be pyrrolidino, methylpyrrolidino, morpholino, thiomorpholino, piperidino, methylpiperidino, N-methylpiperazino, 1,2,3,6-tetrahydropyridyl, homopiperidino, heptamethyleneimino, octamethyleneimino or 3-azabicyclo[3.2.2]nonane.

Another preferred embodiment of the intermediates of Formula III are those having the structure

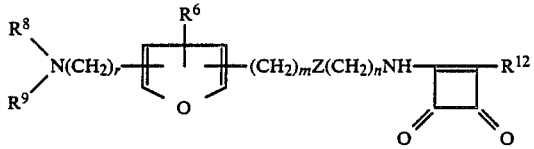
IIIb wherein $R^{12}$ is a conventional leaving group selected from halogen, phenoxy, substituted phenoxy and (lower)alkoxy;

m is an integer of from 0 to 2 inclusive;

n is an integer of from 2 to 5 inclusive;

Z is sulfur, oxygen or methylene;

$R^6$ is hydrogen or (lower)alkyl;

r is an integer of from 1 to 4 inclusive; and $R^8$ and $R^9$ each are independently hydrogen or (lower)alkyl, or $R^8$ and $R^9$, taken together with the nitrogen atom to which they are attached, may be pyrrolidino, methylpyrrolidino, morpholino, thiomorpholino, piperidino, methylpiperidino, N-methylpiperazino, 1,2,3,6-tetrahydropyridyl, homopiperidino, heptamethyleneimino, octamethyleneimino or 3-azabicyclo[3.2.2]nonane.

Another preferred embodiment of the intermediates of Formula III are those having the structure

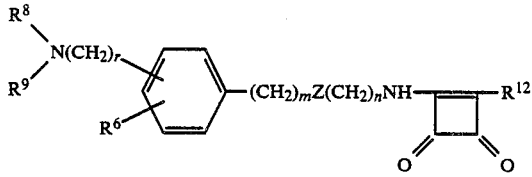
IIIc wherein $R^{12}$ is a conventional leaving group selected from halogen, phenoxy, substituted phenoxy and (lower)alkoxy;

m is an integer of from 0 to 2 inclusive;

n is an integer of from 2 to 5 inclusive;

Z is sulfur, oxygen or methylene;

$R^6$ is hydrogen or (lower)alkyl;

r is an integer of from 1 to 4 inclusive; and $R^8$ and $R^9$ each are independently hydrogen or (lower)alkyl, or $R^8$ and $R^9$, taken together with the nitrogen atom to which they are attached, may be pyrrolidino, methylpyrrolidino, morpholino, thiomorpholino, piperidino, methylpiperidino, N-methylpiperazino, 1,2,3,6-tetrahydropyridyl, homopiperidino, heptamethyleneimino, octamethyleneimino or 3-azabicyclo[3.2.2]nonane.

Another preferred embodiment of the intermediates of Formula III are those having the structure

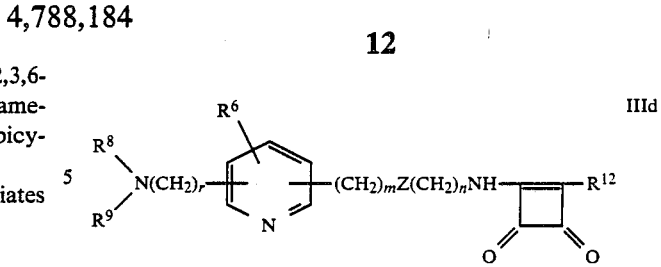
IIId wherein $R^{12}$ is a conventional leaving group selected from halogen, phenoxy, substituted phenoxy and (lower)alkoxy;

m is an integer of from 0 to 2 inclusive;

n is an integer of from 2 to 5 inclusive;

Z is sulfur, oxygen or methylene;

$R^6$ is hydrogen or (lower)alkyl;

r is an integer of from 1 to 4 inclusive; and $R^8$ and $R^9$ each are independently hydrogen or (lower)alkyl; or $R^8$ and $R^9$, taken together with the nitrogen atom to which they are attached, may be pyrrolidino, methylpyrrolidino, morpholino, thiomorpholino, piperidino, methylpiperidino, N-methylpiperazino, 1,2,3,6-tetrahydropyridyl, homopiperidino, heptamethyleneimino, octamethyleneimino or 3-azabicyclo[3.2.2]nonane.

As presently envisaged, the most preferred intermediates of Formula III are .

(a) 1-Methoxy-2-[3-(3-piperidinomethylphenoxy)propylamino]cyclobutene-3,4-dione.

(b) 1-Methoxy-2-{2-[(5-dimethylaminomethyl-2-furyl)methylthio]ethylamino}cyclobutene-3,4-dione.

(c) 1-Methoxy-2-{2-[(5-dimethylaminomethyl-3-thienyl)methylthio]ethylamino}cyclobutene-3,4-dione.

(d) 1-Methoxy-2-{2-[(5-piperidinomethyl-3-thienyl)methylthio]ethylamino}cyclobutene-3,4-dione.

(e) 1-Methoxy-2-[3-(3-dimethylaminomethylphenoxy)propylamino]cyclobutene-3,4-dione.

(f) 1-Methoxy-2-[3-(3-pyrrolidinomethylphenoxy)propylamino]cyclobutene-3,4-dione.

(g) 1-Methoxy-2-{3-[3-(3-methylpyrrolidino)methylphenoxy]propylamino}cyclobutene-3,4-dione.

(h) 1-Methoxy-2-[3-(3-hexamethyleneiminomethylphenoxy)propylamino]cyclobutene-3,4-dione.

(i) 1-Methoxy-2-[3-(3-piperidinomethylthiophenoxy)propylamino]cyclobutene-3,4-dione.

(j) 1-Methoxy-2-[3-(3-heptamethyleneiminomethylphenoxy)propylamino]cyclobutene-3,4-dione.

(k) 1-Methoxy-2-[3-(3-octamethyleneiminomethylphenoxy)propylamino]cyclobutene-3,4-dione.

The starting materials of Formula II used in the preparation of the compounds of this invention are either known or are prepared by methods known in the art. See, for example, the extensive review article by A. H. Schmidt in Synthesis, Pages 961-994 (December 1980) and references cited therein.

For therapeutic use, the pharmacologically active compounds of Formula I will normally be administered as a pharmaceutical composition comprising as the (or an) essential active ingredient at least one such compound in its basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or non-aqueous liquid suspension. The pharmaceutical compositions are prepared by conventional techniques appropriate to the desired preparation.

The dosage of the compounds of this invention will depend not only on such factors as the weight of the patient, but also on the degree of gastric acid inhibition desired and the potency of the particular compound being utilized. The decision as to the particular dosage to be employed is within the discretion of the physician. In the Heidenhain Pouch Dog test described below, cimetidine has an oral $ED_{50}$ of approximately 3.3 $\mu$moles/kg. The usual human adult oral dose of cimetidine is 300 mg, given four times a day. The usual human adult starting oral dosages of the compounds of this invention are readily determined from their oral $ED_{50}$ in this same test. Thus, if the oral $ED_{50}$ is 0.33 $\mu$moles/kg, the usual starting oral dosage would be approximately 30 mg, given four times a day, etc. Similar calculations may be made for iv dosages. These starting dosages (and the number of times administered per day) may, of course, be varied by titration of the dosage to the particular circumstances of the specific patient. With the preferred compounds of this invention, each oral dosage unit will contain the active ingredient in an amount of from about 5 mg to about 300 mg, and most preferably from about 10 mg to about 100 mg. The active ingredient will preferably be administered in equal doses from one to four times a day.

Histamine $H_2$-receptor antagonists have been shown to be effective inhibitors of gastric secretion in animals, including man, Brimblecombe et al., *J. Int. Med. Res.*, 3, 86 (1975). Clinical evaluation of the histamine $H_2$-receptor antagonist cimetidine has shown it to be an effective therapeutic agent in the treatment of peptic ulcer disease, Gray et al., *Lancet*, 1, 8001 (1977). Two of the standard animal models for determining gastric antisecretory activity of histamine $H_2$-antagonists are the Gastric Fistula Rat and the Heidenhain Pouch Dog. The $ED_{50}$'s for some of the compounds of this invention in these two animal models are given in Tables 1 and 2, below.

Determination of Gastric Antisecretory Activity in the Gastric Fistula Rat

Male Long Evans rats weighing about 240–260 grams at the time of cannula implantation are used. The design and implantation of the stainless steel cannula into the anterior wall of the fore-stomach are carried out essentially as described by Pare et al. [Laboratory Animal Science, 27, 244 (1977)]. The fistula components are designed and the operative procedure is carried out exactly as described in the above reference. Post operatively the animals are individually housed in solid bottom cages with sawdust and are allowed food and water ad libitum throughout the entire recovery period. Animals are not used for test purposes for at least 15 days after the operative procedure.

The animals are fasted but allowed water ad libitum for 20 hours before the testing procedure is to begin. Immediately prior to collection, the cannula is opened and the stomach washed gently with 30–40 ml of warm saline or distilled water to remove any residual contents. The catheter is then screwed into the cannula in place of the plugging screw and the rat is placed in a clear plastic rectangular cage measuring 40 cm long, 15 cm wide and 13 cm high. The bottom of the cage has a slit approximately 1.5 cm wide and 25 cm long running down the center to accommodate the catheter which hangs through it. In this way the rat is not restricted and can move freely about the cage during collection periods. The remainder of the assay is carried out as described by Ridley et al. [Research Comm. Chem. Path. Pharm., 17, 365 (1977)].

Gastric secretions collected during the first hour after washing the stomach are discarded as they may be contaminated. For oral evaluation, the catheter is then removed from the cannula and replaced with the plugging screw. Water (2 ml/kg) is administered orally via gastric intubation and the animal is returned to the cage for 45 minutes. After this time the plugging screw is removed and replaced with a catheter to which a small plastic vial has been attached to collect the gastric secretions. A two hour sample is collected (this represents the control secretion), the catheter removed and replaced with the plugging screw. The test drug is now administered orally in a volume of 2 ml/kg via gastric intubation. Forty-five minutes later the plugging screw is again removed, replaced with the catheter attached to a small plastic vial and another 2 hour sample is collected. The secretions in the second sample are compared to those of the control sample in order to determine the effects of the test drug.

When test compounds are to be evaluated parenterally, the animal is injected ip or sc with the test compound vehicle in a volume of 2 ml/kg immediately after discarding the initial 60 minute collection. A two hour sample is collected (control secretion) and the animals are injected either ip or sc with the test compound in a volume of 2 ml/kg. An additional two hour sample is collected and its secretions are compared to those of the control period to determine drug effects.

The samples are centrifuged and placed in a graduated centrifuge tube for volume determination. Titratable acidity is measured by titrating a one ml sample to pH 7.0 with 0.02N NaOH, using an Autoburet and an electrometric pH meter (Radiometer). Titratable acid output is calculated in microequivalents by multiplying the volume in milliliters by the acid concentration in milliequivalents per liter.

Results are expressed as percent inhibition relative to control readings. Dose response curves are constructed and $ED_{50}$ values are calculated by regression analyses. At least three rats are used at each dosage level and a minimum of three dosage levels are utilized for deermination of a dose response curve.

Determination of Gastric Antisecretory Activity in the Heidenhain Pouch Dog

Prior to surgery, hematology and blood chemistry profiles are obtained and an assessment made as to the general health of selected female dogs. Dogs are vaccinated with Tissue Vax 5 (DHLP—Pitman-Moore) and housed in general animal quarters for four weeks' observation so incipient diseases may become apparent. Dogs are fasted with water ad libitum 24 hours prior to surgery.

Anesthesia is induced with Sodium Pentothal (Abbott) 25–30 mg/kg iv. Subsequent anesthesia is maintained with methoxyflurane (Pitman-Moore). A midline linea alba incision from xiphoid to umbilicus provides good exposure and ease of closure. The stomach is pulled up into the operative field, the greater curvature stretched out at multiple points and clamps placed along the selected line of incision. The pouch is made from the corpus of the stomach so that true parietal cell juice is obtained. About 30% of the corpus volume is resected. The cannula is made of light-weight, biologically-inert material such as nylon or Delrin with dimensions and attachments after DeVito and Harkins [J. Appl. Physiol., 14, 138 (1959)]. Post operatively, dogs are medicated with antibiotics and an analgesic. They are allowed 2-3 months for recovery. Experiments are carried out in the following way: Dogs are fasted overnight (~18 hours) with water ad libitum prior to each experiment. The dogs are placed in a sling and a saphenous vein cannnulated for drug administration. Histamine as the base (100 μg/kg/hr) and chlorpheniramine maleate (0.25 mg/kg/hr) are infused continuously (in a volume of 6 ml/hr) with a Harvard infusion pump.

Ninety minutes' infusion are allowed for the dogs to reach a steady state of acid output. At this time the drug or normal saline (control) is administered concomitantly with the secretagogue in a volume of 0.5 ml/kg over a 30 second period. When oral studies are to be carried out, the drug is administered via gastric gavage in a volume of 5 ml/kg. Infusion of the secretagogue is continued and 15 minute samples of the gastric juice are taken for 4.5 hours. Each sample is measured to the nearest 0.5 ml and titratable acidity is determined by titrating a 1 ml sample to pH 7.0 with 0.2N NaOH, using an Autoburet and an electrometric pH meter (Radiometer). Titratable acid output is calculated in microequivalents by multiplying the volume in milliliters by the acid concentration in milliequivalents per liter.

Results are expressed as percent inhibition relative to control readings. Dose response curves are constructed and $ED_{50}$ values are calculated by regression analyses. From 3 to 5 dogs are used at each dose level and a minimum of three dosage levels are utilized for determination of a dose response curve.

Celite is a registered trademark of the Johns-Manville Products Corporation for diatomaceous earth.

In the following examples, all temperatures are given in degrees Centigrade.

TABLE 1

Gastric Antisecretory Activity in the Gastric Fistula Rat

| Compound | $ED_{50}$ sc [μmoles/kg] | Potency Ratio [cimetidine = 1.0] |
|---|---|---|
| Cimetidine | 3.8 (2.3–5.5)* | 1.0 |
| Compound of Example 1 | 0.023 (0.011–0.037) | 162 (77–328)* |
| Compound of Example 2 | <1 | >4 |
| Compound of Example 3 | ~4 | ~1 |
| Compound of Example 9 | 0.055 (0.016–0.14) | 61 (20–204) |
| Compound of Example 10i | 0.08 (0.04–0.16) | 48 (21–97) |
| Compound of Example 10j | 0.044 (0.019–0.09) | 88 (36–211) |
| Compound of Example 10m | 0.7 (0.36–1.4) | 5.4 (2.1–12) |
| Compound of Example 11 | 0.067 (0.02–0.18) | 50 (15–169) |
| Compound of Example 12 | 0.094 (0.046–0.17) | 44 (22–90) |
| Compound of Example 14d | 0.031 (0.016–0.056) | 124 (62–243) |

*numbers in parentheses are 95% confidence limits

TABLE 2

Gastric Antisecretory Activity in the Heidenhain Pouch Dog

| Compound | $ED_{50}$ [μmoles/kg] | Potency Ratio [cimetidine = 1.0] |
|---|---|---|
| (INTRAVENOUS) | | |
| Cimetidine | 2.18 (1.48–2.95)* | 1.0 |
| Compound of Example 1 | 0.024 (0.019–0.029) | 87 (62–117)* |
| Compound of Example 2 | | ~20 |
| Compound of Example 9 | | ~40 |
| Compound of Example 10i | | >40 |
| (ORAL) | | |
| Cimetidine | 3.29 (1.05–5.19) | 1.0 |
| Compound of Example 1 | 0.16 (0.10–0.22) | 25 (14–40) |
| Compound of Example 9 | | ~20 |

*numbers in parentheses are 95% confidence limits

EXAMPLE 1

1-Amino-2-[3-(3-piperidinomethylphenoxy)-propylamino]cyclobutene-3,4-dione

A solution of 3-(3-piperidinomethylphenoxy)propylamine (from the dihydrochloride, 4.46 g; 13.9 mmoles) [prepared according to published U.K. patent application No. 2,023,133] in 40 mL of methanol was added all at once to a solution of 1,2-dimethoxycyclobutene-3,4-dione (1.97 g; 13.9 mmoles) in 40 mL of methanol that had been cooled to 5° in an ice-water bath. After 2 hours at ambient temperature, the solution was cooled to 5° and excess anhydrous ammonia was bubbled into the solution for 5 minutes. The mixture was stirred at ambient temperature for 18 hours and then filtered to give 4.35 g of product.

The product (4.20 g; 12.2 mmoles) was suspended in 40 mL of 95% aqueous ethanol and 6.11 mL (12.2 mmoles) of aqueous 2.0N HCl was added with stirring. The solution was filtered through Celite, cooled at 0° for 17 hours, and then filtered to give 4.33 g of the title compound as its hydrochloride salt, mp 254°–257°.

Anal. Calc'd. for $C_{19}H_{26}ClN_3O_3$: C, 60.08; H, 6.90, N, 11.06; Cl, 9.33. Found (corr. for 0.28% $H_2O$): C, 59.73; H, 6.97; N, 11.14; Cl, 9.36.

EXAMPLE 2

1-Amino-2-{2-[(5-dimethylaminomethyl-2-furyl)methylthio]ethylamino}cyclobutene-3,4-dione A solution of 2-[(5-dimethylaminomethyl-2-furyl)methylthio]ethylamine (2.89 g; 13.5 mmoles) [prepared according to the procedure described in Belgian Pat. No. 857,388] in 30 mL of methanol was added dropwise over a period of 30 minutes to a cold (5°) stirred solution of 1,2-dimethoxycyclobutene-3,4-dione (1.92 g; 13.5 mmoles) in 50 mL of methanol. After 3 hours at ambient temperature, the solution was cooled to 5° and excess anhydrous ammonia was bubbled into the solution for 5 minutes. The mixture was stirred at ambient temperature for 18 hours and then filtered to give 2.48 g of the title compound, mp 227°–230° (dec.).

An analytical sample was prepared by recrystallization from 95% aqueous ethanol and then from methanol, and was dried in vacuo over $P_2O_5$ for 18 hours to give the title compound as a non-friable sticky solid; the NMR spectrum (100 MHz) in $d_6$ dimethylsulfoxide showed the presence of approximately 0.2 moles of methanol.

Anal. Calc'd. for $C_{14}H_{19}N_3O_3S \cdot 0.2CH_4O$: C, 54.01; H, 6.32; N, 13.31; S, 10.15. Found (corr. for 0.54% $H_2O$): C, 53.72; H, 6.07; N, 14.01; S, 10.51.

EXAMPLE 3

1-Amino-2-{2-[(5-dimethylaminomethyl-2-thienyl)methylthio]ethylamino}cyclobutene-3,4-dione A solution of 2-[(5-dimethylaminomethyl-2-thienyl)methylthio]ethylamine (2.06 g; 8.94 mmoles) [prepared according to the procedure described in Belgian Pat. No. 867,105] in 20 mL of methanol was added all at once to a cold (5°) solution of 1,2-dimethoxycyclobutene-3,4-dione (1.27 g; 8.94 mmoles) in 20 mL of methanol. After 3.5 hours at ambient temperature, the solution was cooled to 5° and excess anhydrous ammonia was bubbled into the solution for 5 minutes. The mixture was stirred for 18 hours at ambient temperature and then filtered to give 2.66 g of product. Recrystallization from 95% aqueous ethanol yielded the title compound, mp 240°–243° (dec.).

Anal. Calc'd. for $C_{14}H_{19}N_3O_2S_2$: C, 51.67; H, 5.88; N, 12.91; S, 19.70. Found: C, 51.60; H, 5.76; N, 12.97; S, 19.69.

EXAMPLE 4

2-{2-[(5-Dimethylaminomethyl-2-furyl)methylthio]ethylamino}-1-methylaminocyclobutene-3,4-dione A solution of 2-[(5-dimethylaminomethyl-2-furyl)methylthio]ethylamine (2.89 g; 13.5 mmoles) in 30 mL of methanol was added all at once to a cold (5°) solution of 1,2-dimethoxycyclobutene-3,4-dione (1.92 g; 13.5 mmoles) in 50 mL of methanol. After 3 hours at ambient temperature, the solution was cooled to 5° and excess anhydrous methylamine was bubbled into the solution for 5 minutes. The mixture was stirred for 18 hours at ambient temperature, evaporated under reduced pressure and then triturated with acetonitrile and filtered to give 2.9 g of crude product. The product was placed on 40 g of silica gel (230–400 mesh) and chromatographed by flash chromatography using a gradient elution of methanol-acetonitrile. The appropriate fractions were evaporated, then combined in methanol, treated with charcoal, filtered and evaporated to near dryness. The solid was triturated with acetonitrile and filtered to give the title compound, m.p. 176°–177.5°.

Anal. Calc'd for $C_{15}H_{21}N_3O_3S$: C, 55.71; H, 6.54; N, 12.99; S, 9.91. Found (corr. for 1.86% $H_2O$): C, 55.46; H, 6.39; N, 13.14; S, 10.30.

EXAMPLE 5

2-{2-[(5-Dimethylaminomethyl-2-thienyl)methylthio]ethylamino}-1-methylaminocyclobutene-3,4-dione A solution of 2-[(5-dimethylaminomethyl-2-thienyl)methylthio]ethylamine (1.32 g; 5.73 mmoles) in 20 mL of methanol was added to a cold (5°) solution of 1,2-dimethoxycyclobutene-3,4-dione (814 mg; 5.73 mmoles) in 15 mL of methanol. After 3.5 hours at ambient temperature, the solution was cooled to 5° and excess anhydrous methylamine was bubbled into the solution for 5 minutes. The mixture was stirred for 70 hours at ambient temperature and then filtered to give 1.38 g of product. Recrystallization from ethanol yielded the title compound, m.p. 185°–187°.

Anal. Calc'd for $C_{15}H_{21}N_3O_2S_2$: C, 53.07; H, 6.23; N, 12.38; S, 18.89. Found: C, 53.18; H, 6.21; N, 12.25; S, 18.94.

EXAMPLE 6

1-Amino-2-{2-[(5-dimethylaminomethyl-4-methyl-2-thienyl)methylthio]ethylamino}cyclobutene-3,4-dione A mixture of 2-[(5-dimethylaminomethyl-4-methyl-2-thienyl)methylthio]ethylamine (3.0 g; 12.3 mmoles) [prepared according to the procedure described in published United Kingdom patent application No. 2,063,875] and 1-amino-2-methoxycyclobutene-3,4-dione (1.56 g; 12.3 mmoles) in 50 mL of methanol was stirred at ambient temperature for 18 hours and then filtered to give 3.72 g of product. Recrystallization from 95% aqueous ethanol gave 3.1 g of the title compound.

The product (3.1 g; 9.13 mmoles) was suspended in 40 mL of methanol and 1.52 mL of aqueous 6.0N HCl was added with stirring. The mixture was filtered and the solid was recrystallized from aqueous methanol to give the title compound as its hydrochloride salt, m.p. 202°–205°.

Anal. Calc'd for $C_{15}H_{21}N_3O_2S_2 \cdot HCl$: C, 47.93; H, 5.90; N, 11.18; S, 17.06; Cl, 9.43. Found (corr. for 0.38% $H_2O$): C, 47.74; H, 5.79; N, 11.41; S, 17.21; Cl, 9.42.

EXAMPLE 7

1-Amino-2-{2-[(5-piperidinomethyl-4-methyl-2-thienyl)methylthio]ethylamino}cyclobutene-3,4-dione The general procedure of Example 6 was repeated except that the 2-[(5-dimethylaminomethyl-4-methyl-2-thienyl)methylthio]ethylamine utilized therein was replaced by an equimolar amount of 2-[(5-piperidinomethyl-4-methyl-2-thienyl)methylthio]ethylamine [prepared according to the procedure described in published United Kingdom patent application No. 2,063,875]. The product (3.64 g; 9.6 mmoles) was suspended in 50 mL of ethanol and 4.8 mL of aqueous 2.0N HCl was added with stirring. The mixture was filtered and the solid was recrystallized from aqueous ethanol to give the title compound as its hydrochloride salt, m.p. 150°–157°.

Anal. Calc'd for $C_{18}H_{25}N_3O_3S_2 \cdot HCl$: C, 51.97; H, 6.30; N, 10.10; S, 15.41; Cl, 8.52. Found (corr. for 1.58% $H_2O$): C, 52.05; H, 6.33; N, 10.37; S, 15.24; Cl, 8.16.

EXAMPLE 8

1-Amino-2-[3-(3-piperidinomethylphenoxy)propylamino]cyclobutene-3,4-dione

A solution of 3-(3-piperidinomethylphenoxy)propylamine from the dihydrochloride, 43.37 g; 0.135 mmoles) in 250 mL of methanol was added to a suspension of 1-amino-2-methoxycyclobutene-3,4-dione (17.16 g; 0.135 moles) in 350 mL of methanol and stirred at ambient temperature. After 22 hours, the mixture was filtered to give 38.0 g of product.

The product (38.0 g; 0.111 moles) was suspended in 375 mL of aqueous 95% ethanol and 55.3 mL of aqueous 2.0N HCl was added with stirring. The mixture was filtered to give 40.5 g of the title compound as its hydrochloride salt, which is identical to the product prepared in Example 1.

The product was further purified by dissolving in 30% aqueous ethanol then filtered through a pad of silica gel and carbon, evaporated and the solid recrystallized from aqueous ethanol to yield a colorless hydrochloride salt of the title compound, m.p. 257°–259°.

Anal. Calc'd for $C_{19}H_{25}N_3O_3HCl$: C, 60.08; H, 6.90; N, 11.06; Cl, 9.33. Found: C, 59.82; H, 7.10; N, 10.87; Cl, 9.47.

EXAMPLE 9

1-Amino-2-[3-(3-dimethylaminomethylphenoxy)-propylamino]cyclobutene-3,4-dione

A mixture of 3-(3-dimethylaminomethylphenoxy)-propylamine (1.41 g; 6.77 mmoles) [prepared according to the procedure described in Belgian Pat. No. 867,106] and 1-amino-2-methoxycyclobutene-3,4-dione (0.86 g; 6.77 mmoles) in 40 mL of methanol was stirred at ambient temperature for 20 hours and then filtered to give 1.95 g of the title compound.

The product (1.95 g; 6.43 mmoles) was suspended in 35 mL of ethanol and 3.21 mL of 2.0N aqueous HCl was added with stirring. The mixture was filtered and the solid was recrystallized from aqueous ethanol to give the hydrochloride salt of the title compound, m.p. 205°–207°.

Anal. Calc'd for $C_{16}H_{21}N_3O_3HCl$: C, 56.55; H, 6.52; N, 12.37; Cl, 10.43. Found: C, 56.25; H, 6.56; N, 12.36; Cl, 10.27.

EXAMPLE 10

The general procedure of Example 9 is repeated, except that the 3-(3-dimethylaminomethylphenoxy)-propylamine utilized therein is replaced by an equimolar amount of (a) 3-(3-pyrrolidinomethylphenoxy)propylamine,
(b) 3-[3-(2-methylpyrrolidino)methylphenoxy]propylamine,
(c) 3-[3-(3-methylpyrrolidino)methylphenoxy]propylamine,
(d) 3-[3-(4-methylpiperidino)methylphenoxy]propylamine,
(e) 3-(3-morpholinomethylphenoxy)propylamine,
(f) 3-[3-(4-hydroxypiperidino)methylphenoxy]propylamine,
(g) 3-[3-(N-methylpiperazino)methylphenoxy]propylamine,
(h) 3-[3-(1,2,3,6-tetrahydro-1-pyridyl)methylphenoxy]propylamine,
(i) 3-(3-hexamethyleneiminomethylphenoxy)propylamine,
(j) 3-(3-heptamethyleneiminomethylphenoxy)propylamine,
(k) 4-(3-piperidinomethylphenoxy)butylamine,
(l) 5-(3-piperidinomethylphenoxy)pentylamine,
(m) 3-(3-octamethyleneiminomethylphenoxy)propylamine,
(n) 3-[3-(3-azabicyclo[3.2.2]non-3-yl)methylphenoxy]propylamine and
(o) 3-[3-(3-pyrrolino)methylphenoxy]propylamine, respectively, and there is thereby produced
(a) 1-amino-2-[3-(3-pyrrolidinomethylphenoxy)-propylamino]cyclobutene-3,4-dione as its hydrochloride salt, m.p. 192.5°–195°.

Anal. Calc'd for $C_{18}H_{23}N_3O_3HCl$: C, 59.10; H, 6.61; N, 11.49; Cl, 9.69. Found (corr. for 0.55% $H_2O$): C, 58.92; H, 6.73; N, 11.61; Cl, 9.41.

(b) 1-amino-2-3-[3-(2-methylpyrrolidino)metylphenoxy]propylaminocyclobutene-3,4-dione as its hydrochloride salt, m.p. 210°–212°.

Anal. Calc'd for $C_{19}H_{25}N_3O_3HCl$: C, 60.08; H, 6.90; N, 11.06; Cl, 9.33. Found: C, 59.97; H, 6.92; N, 10.88; Cl, 9.46.

(c) 1-amino-2-{3-[3-(3-methylpyrrolidino)methylphenoxy]propylamino}cyclobutene-3,4-dione as its hydrochloride salt, m.p. 184.5°–187°.

Anal. Calc'd for $C_{19}H_{25}N_3O_3HCl$: C, 60.08; H, 6.90; N, 11.06; Cl, 9.33. Found: (corr. for 0.26% $H_2O$): C, 60.43; H, 7.02; N, 11.03; Cl, 9.31.

(d) 1-amino-2-{3-[3-(4-methylpiperidino)methylphenoxy]propylamino}cyclobutene-3,4-dione,
(e) 1-amino-2-[3-(3-morpholinomethylphenoxy)-propylamino]cyclobutene-3,4-dione,
(f) 1-amino-2-{3-[3-(4-hydroxypiperidino)methylphenoxy]propylamino}cyclobutene-3,4-dione,
(g) 1-amino-2-{3-[3-(N-methylpiperazino)methylphenoxy]propylamino}cyclobutene-3,4-dione,
(h) 1-amino-2-{3-[3-(1,2,3,6-tetrahydro-1-pyridyl)methylphenoxy]propylamino}cyclobutene-3,4-dione, m.p. 213°–215° (dec.),
(i) 1-amino-2-[3-(3-hexamethyleneiminomethylphenoxy)propylamino]cyclobutene-3,4-dione as its hydrochloride salt, m.p. 200°–202°.

Anal. Calc'd for $C_{20}H_{27}N_3O_3HCl$: C, 60.98; H, 7.16; N, 10.67; Cl, 9.00. Found (corr. for 0.28% $H_2O$): C, 61.25; H, 7.14; N, 10.55; Cl, 8.61.

(j) 1-amino-2-[3-(3-heptamethyleneiminomethylphenoxy)propylamino]cyclobutene-3,4-dione, m.p. undefined, gradual decomposition ~200°–240°.

Anal. Calc'd for $C_{21}H_{29}N_3O_3$: C, 67.90; H, 7.87; N, 11.31. Found: C, 66.44; H, 7.74; N, 11.33.

(k) 1-amino-2-[4-(3-piperidinomethylphenoxy)-butylamino]cyclobutene-3,4-dione,
(l) 1-amino-2-[5-(3-piperidinomethylphenoxy)pentylamino]cyclobutene-3,4-dione,
(m) 1-amino-2-[3-(3-octamethyleneiminomethylphenoxy)propylamino]cyclobutene-3,4-dione, m.p. undefined.

Anal. Calc'd for $C_{22}H_{31}N_3O_3$: C, 68.54; H, 8.11; N, 10.90. Found: C, 68.42; H, 8.42; N, 11.10.

(n) 1-amino-2-{3-[3-(3-azabicyclo[3.2.2]non-3-yl)methylphenoxy]propylamino}cyclobutene-3,4-dione as its hydrochloride salt, m.p. 162°–164° and
(o) 1-amino-2-{3-[3-(3-pyrrolino)methylphenoxy]propylamino}cyclobutene-3,4-dione, respectively.

EXAMPLE 11

1-Methylamino-2-[3-(3-piperidinomethylphenoxy)-propylamino]cyclobutene-3,4-dione A solution of 3-(3-piperidinomethylphenoxy)propylamine (from the dihydrochloride, 3.21 g; 10.0 mmoles) in 40 mL of methanol was added to a solution of 1,2-dimethoxycyclobutene-3,4-dione (1.42 g; 10.0 mmoles) in 40 mL of methanol. After 1 hour at 10° and 30 minutes at ambient temperature, the solution was cooled to 5° and excess anhydrous methylamine was bubbled into the solution for 5 minutes. The mixture was stirred for 17 hours at ambient temperature and then filtered to give 2.77 g of product.

The product (2.77 g) was suspended in 40 mL of ethanol and 4.07 mL (8.1 mmoles) of aqueous 2N HCl was added with stirring to yield the hydrochloride salt of the title compound, m.p. 194°–198°.

Anal. Calc'd for $C_{20}H_{27}N_3O_3 \cdot HCl$: C, 60.99; H, 7.16; N, 10.67. Found (corr. for 1.35% $H_2O$): C, 60.63; H, 6.96; N, 10.71.

EXAMPLE 12

2-[3-(3-Piperidinomethylphenoxy)propylamino]-1-(3-pyridyl)methylaminocyclobutene-3,4-dione The general procedure of Example 11 was repeated, except that the methylamine utilized therein was replaced by 1.08 g (10.0 mmoles) of 3-aminomethylpyridine. The crude product was placed on 65 g of silica gel (230–400 mesh) and chromatographed by flash chromatography using a gradient elution of methanolmethylene chloride containing 1% $NH_4OH$. The appropriate fractions were combined, evaporated and the solid residue recrystallized from methanol to give the title compound, m.p. 174°–178.5°.

Anal. Calc'd for $C_{25}H_{30}N_4O_3$: C, 69.10; H, 6.96; N, 12.89. Found (corr. for 0.52% $H_2O$): C, 68.80; H, 7.03; N, 12.74.

EXAMPLE 13

2-[3-(3-Piperidinomethylphenoxy)propylamino]-1-propylaminocyclobutene-3,4-dione

The general procedure of Example 11 was repeated, except that the methylamine utilized therein was replaced by 4.0 mL (48.7 mmoles) of propylamine. The crude product was placed on 60 g of silica gel (230–400 mesh) and chromatographed by flash chromatography using a gradient elution of methanol-methylene chloride. The appropriate fractions were combined and the solid residue recrystallized from methanol to yield the title compound, m.p. 158°–160°.

Anal. Calc'd for $C_{22}H_{31}N_3O_3$: C, 68.54; H, 8.11; N, 10.90. Found: C, 68.11; H, 8.25; N, 11.21.

EXAMPLE 14

The general procedure of Example 12 is repeated, except that the 3-aminomethylpyridine utilized therein is replaced by an excess molar amount of
- (a) ethylamine,
- (b) n-butylamine,
- (c) allylamine,
- (d) propargylamine,
- (e) benzylamine and
- (f) 6-methyl-3-aminomethylpyridine, respectively, and there is thereby produced
(a) 1-ethylamino-2-[3-(3-piperidinomethylphenoxy)-propylamino]cyclobutene-3,4-dione,
(b) 1-butylamino-2-[3-(3-piperidinomethylphenoxy)-propylamino]cyclobutene-3,4-dione,
(c) 1-allylamino-2-[3-(3-piperidinomethylphenoxy)-propylamino]cyclobutene-3,4-dione, m.p. 158°–159.5°.

Anal. Calc'd for $C_{22}H_{29}N_3O_3$: C, 68.90; H, 7.62; N, 10.96. Found: C, 68.81; H, 7.70; N, 10.72.

(d) 2-[3-(3-piperidinomethylphenoxy)propylamino]-1-(2-propynylamino)cyclobutene-3,4-dione, m.p. 158°–160°.

Anal. Calc'd for $C_{22}H_{27}N_3O_3$: C, 69.27; H, 7.13; N, 11.02. Found: C, 69.26; H, 7.25; N, 10.78.

(e) 1-benzylamino-2-[3-(3-piperidinomethylphenoxy)-propylamino]cyclobutene-3,4-dione hydrochloride, m.p. 136°–140°.

Anal. Calc'd for $C_{26}H_{31}N_3O_3HCl$: C, 66.44; H, 6.86; N, 8.94; Cl, 7.54. Found: C, 65.41; H, 7.08; N, 8.83; Cl, 7.67.

and (f) 1-(6-methyl-3-pyridyl)methylamino-2-[3-(3-piperidinomethylphenoxy)propylamino]cyclobutene-3,4-dione, respectively.

EXAMPLE 15

1-Amino-2-[3-(6-piperidinomethyl-2-pyridyloxy)-propylamino]cyclobutene-3,4-dione A. 2-Chloro-6-piperidinomethylpyridine To 2-chloro-6-methylpyridine (50.0 g, 0.392 mole) in 393 mL of carbon tetrachloride was added N-bromosuccinimide (87.2 g, 0.49 mole) and 1.0 g of benzoyl peroxide. The mixture was stirred at reflux for 22 hours, cooled to 10° and filtered. The chilled filtrate then was treated slowly with piperidine (83.5 g, 0.98 mole) and allowed to stir at ambient temperature for 18 hours. After removal of the piperidine hydrobromide by filtration, the filtrate was concentrated to about half volume and extracted with 6N HCl (65 mL) and 3N HCl (40 mL). The acid extracts were made basic with 40% sodium hydroxide and the product was extracted into methylene chloride. The solvent was evaporated and the residue distilled to yield 41% of the title compound as a colorless oil, b.p. 101°–103°/0.45 mm Hg.

Anal. Calc'd for $C_{11}H_{15}ClN_2$: C, 62.71; H, 7.18; 13.29; Cl, 16.82. Found: C, 61.71; H, 7.31; 13.63; Cl, 71.20.

B. N-[3-(6-Piperidinomethyl-2-pyridyloxy)propyl]-formamide

3-Aminopropanol (12.84 g, 0.171 mole) was added to a suspension of 50% sodium hydride in mineral oil (7.96 g, 0.166 mole) in 180 mL of dry DMF and the mixture was warmed to 80°–83°. A solution of 2-chloro-6-piperidinomethylpyridine (34.0 g, 0.161 mole) [prepared in Step A] in 180 mL of dry DMF was then added dropwise and when complete, the temperature was raised to 125°–128° for 3 hours followed by 17 hours at ambient temperature. The precipitated salts were removed by filtration and the solvent stripped under vacuum. The oily residue was dissolved in methylene chloride, washed with water, dried and the solvent evaporated. This residue was redissolved in acetonitrile and extracted with skelly B. After removing the solvent the crude oil was purified by flash chromatography on 270 g of silica gel (230–400 mesh) using a gradient elution of methanol-methylene chloride and evaporated to give the title product as a yellow oil, 21.63 g (48.4%).

C. 3-(6-Piperidinomethyl-2-pyridyloxy)propylamine

N-[3-(6-Piperidinomethyl-2-pyridyloxy)propyl]formamide (19.6 g, 70.7 mmoles) [prepared in Step B] was added to a solution of 85% potassium hydroxide pellets (18.63 g, 0.332 mole) dissolved in 180 mL of methanol and the solution was heated at gentle reflux for 20 hours. The solvent was stripped in vacuum and the residue partially purified by redissolving in about 180 mL of 20% methanol-methylene chloride and passing through a pad of 38 g of silica gel. The silica was washed with an additional 120 mL of eluant and the combined filtrates were evaporated to an amber oil. Final purification was effected by flash chromatography on 120 g of silica gel (230–400 mesh) using a gradient elution of methanol-methylene chloride containing 0.5% $NH_4OH$. The title compound was obtained as a yellow oil in 63% yield.

D. 1-Amino-2-[3-(6-piperidinomethyl-2-pyridyloxy)-propylamino]cyclobutene-3,4-dione A mixture of 3-(6-piperidinomethyl-2-pyridyloxy)-propylamine (2.5 g, 10 mmoles) [prepared in Step C] and 1-amino-2-methoxycyclobutene-3,4-dione (1.27 g, 10 mmoles) in 35 mL of methanol was stirred at ambient temperature for 18 hours and filtered to give 2.71 g of product.

The product (2.71 g, 7.87 mmoles) was suspended in 35 mL of absolute ethanol and 7.87 mL of aqueous 6.0N HCl was added with stirring. After 64 hours at 0° the salt was collected by filtration and recrystallized from aqueous ethanol to give the hydrochloride salt of the title compound, m.p. 255°–258°.

Anal. Calc'd for $C_{18}H_{24}N_4O_3HCl$: C, 56.77; H, 6.61; N, 14.71; Cl, 9.31. Found: C, 56.71; H, 6.80; N, 14.41; Cl, 9.98.

EXAMPLE 16

1-Amino-2-[3-(6-dimethylaminomethyl-2-pyridyloxy)-propylamino]cyclobutene-3,4-dione The general procedure of Example 15 was repeated, except that the piperidine utilized in Step A was replaced with an excess of anhydrous dimethylamine. The product (2.26 g, 7.43 mmoles) was suspended in 40 mL of 95% ethanol and 7.43 mL of aqueous 2.0N HCl was added with stirring. After evaporating most of the solvent, the residue was triturated under isopropyl alcohol and recrystallized from aqueous ethanol to give the hydrochloride salt of the title compound, m.p. 230°–234° (dec.).

Anal. Calc'd for $C_{15}H_{20}N_4O_3HCl$: C, 52.87; H, 6.21; N, 16.44; Cl, 10.40. Found: C, 51.52; H, 5.98; N, 16.64; Cl, 10.88.

EXAMPLE 17

1-Amino-2-[2-(3-piperidinomethylthiophenoxy)ethylamino]cyclobutene-3,4-dione

A. m-Dithiobenzoyl chloride

A mixture of m-dithiobenzoic acid (20.8 g, 67.9 mmoles) [prepared according to the procedure described in *J. Chem. Soc.*, London, 119, 1792 (1921)] and thionyl chloride (200 mL) was refluxed for four hours, filtered and the excess $SOCl_2$ removed in vacuum.

B. Dithio bis-3,3'-N,N-di(piperidino)benzenecarboxamide

The crude product from Step A, dissolved in 100 mL of tetrahydrofuran, was added dropwise at 3° to a solution of piperidine (25.1 g, 0.29 mole) in 500 mL of tetrahydrofuran. The mixture was stirred at ambient temperature for 76 hours and poured into 1500 mL of dilute HCl (ca. 2N). After one hour the product was extracted into ether and washed sequentially with water, aqueous 1N NaOH and water. The solvent was evaporated to leave 26.4 g of the title compound.

C. 3-(piperidinomethyl)thiophenol

To a suspension of lithium aluminum hydride (45.3 g, 1.19 moles) in 2200 mL of ether was added, dropwise under nitrogen, a solution of dithio bis-3,3'-N,N-di(piperidino)benzenecarboxamide (141.5 g, 0.32 mole) [prepared in Step B] in 2200 mL of ether and the mixture was stirred at ambient temperature for 20 hours. The mixture was decomposed by the addition of saturated sodium sulfate solution and filtered. The filter cake was stirred with 3000 mL of water and a solution of citric acid monohydrate (550 g, 2.62 moles) in 550 mL of water was added. The pH of the solution was adjusted to about 2 with 12N HCl and then to pH 8 with concentrated ammonium hydroxide. The solution was exhaustively extracted with ether to yield 120 g of product.

An aliquot of the title compound was recrystallized from isopropyl alcohol, m.p. 121°–123°; Mass spectrum 206 (M+).

Anal. Calc'd for $C_{12}H_{17}NS$: C, 69.56; H, 8.21; N, 6.76; S, 15.46. Found: C, 69.02; H, 8.03; N, 6.67; S, 15.06.

D. N-{2-[3-(Piperidinomethyl)thiophenoxy]ethyl}phthalimide

A mixture of 3-(piperidinomethyl)thiophenol (2.07 g, 10 mmoles) [prepared in Step C] and N-(2-bromoethyl)phthalimide (2.41 g, 9.5 mmoles) in 10 mL of dry DMF was stirred at ambient temperature for 84 hours. The solvent was evaporated under reduced pressure and the crude oil was flask chromatographed on 100 g of silica gel (230–400 mesh) using 2.5% methanol in methylene chloride with 0.2% $NH_4OH$ as the eluant. The appropriate fractions were combined and evaporated to give an oil that crystallized under ether. Recrystallization from acetonitrile yielded 1.2 g of the hydrobromide salt of the title compound, m.p. 180°–181.5°.

Anal. Calc's for $C_{22}H_{24}N_2O_2SHBr$: C, 57.26; H, 5.46; N, 6.07; Br, 17.32; S, 6.95. Found: C, 56.98; H, 5.43; N, 6.30; Br, 17.51; S, 7.10.

E. 2-(3-Piperidinomethylthiophenoxy)ethylamine

Anhydrous hydrazine (1.79 g, 56.0 mmoles) was added to a suspension of N-}2-[3-(piperidinomethyl)thiophenoxy]ethyl}phthalimide hydrobromide (5.17 g, 11.2 mmoles) [prepared in Step D] in 200 mL of 95% ethanol, stirred at ambient temperature for 18 hours and filtered. The filtrate was stripped and the semi-solid residue was stirred with several portions of ether. Evaporation of the solvent gave 2.8 g of title compound as a yellow oil.

F. 1-Amino-2-[2-(3-piperidinomethylthiophenoxy)ethylamino]cyclobutene-3,4-dione

The crude amine prepared in Step E (1.4 g, 4.05 mmoles) in 40 mL of methanol was added to a suspension of 1-amino-2-methoxycyclobutene-3,4-dione (0.515 g, 4.05 mmoles) in 100 mL of methanol. The mixture was stirred for 20 hours at ambient temperature and then filtered to give 0.8136 g of product. A second crop was obtained from the concentrated mother liquor and the combined lots were recrystallized from methanol to yield 0.786 g (56%) of the title compound, m.p. 228°–230° (dec.).

Anal. Calc'd for $C_{18}H_{23}N_3O_2S$: C, 62.58; H, 6.71; N, 12.16; S, 9.28. Found: C, 62.17; H, 6.36; N, 12.59; S, 9.60.

EXAMPLE 18

1-Amino-2-[3-(3-piperidinomethylthiophenoxy)-propylamino]cyclobutene-3,4-dione

A. N-{3-[3-(Piperidinomethyl)thiophenoxy]propyl}phthalimide

The general procedure of Example 17, Step D, was repeated, except the N-(2-bromoethyl)phthalimide utilized therein was replaced with an equimolar amount of N-(3-bromopropyl)phthalimide. The chromatographed product was recrystallized from isopropyl alcohol to give the title compound as its hydrobromide salt, m.p. 188°–192°.

Anal. Calc'd for $C_{23}H_{26}N_2O_2SHBr$: C, 58.10; H, 5.72; N, 5.89; Br, 16.81. Found: C, 57.79; H, 5.41; N, 5.73; Br, 16.80.

B. 3-(3-Piperidinomethylthiophenoxy)propylamine

To a solution of N-{3-[3-(piperidinomethyl)thiophenoxy]propyl}phthalimide hydrobromide (58.0 g, 0.12 mole) [prepared in Step A] in 1650 mL of 95% ethanol was added hydrazine hydrate (26.9 g, 0.54 mole) and the reaction mixture was heated at 45° for 4.5 hours. The mixture was diluted with 500 mL of ether, filtered and the filtrate evaporated to dryness to give the title compound as an amber oil (14.1 g). An aliquot was distilled to a colorless oil, b.p. 154°–155°/0.15 mm Hg.

Anal. Calc'd for $C_{15}H_{24}N_2S$: C, 68.13; H, 9.15; N, 10.59. Found: C, 67.37; H, 9.07; N, 10.94.

C. 1-Amino-2-[3-(3-piperidinomethylthiophenoxy)-propylamino]cyclobutene-3,4-dione 1-Amino-2-methoxycyclobutene-3,4-dione (1.20 g, 9.5 mmoles) was added to a solution of the crude amine prepared in Step B (2.50 g, 9.5 mmoles) in 75 mL of methanol and the mixture was stirred at ambient temperature for 16 hours. The precipitate was filtered to give 2.82 g of crude product.

The crude solid (2.82 g, 7.84 mmoles) was suspended in 30 mL of 95% ethanol and 4.0 mL of aqueous 2.0N HCl was added with stirring. After ca. 15 minutes 40 mL of acetone was added and the mixture stored at ambient temperature for 16 hours. The precipitate was recrystallized from aqueous ethanol to yield 1.64 g of the hydrochloride salt of the title compound, m.p. 236°–237.5°.

Anal. Calc'd for $C_{19}H_{25}N_3O_3S \cdot HCl$: C, 57.64; H, 6.62; N, 10.61; S, 8.10; Cl, 8.95. Found: C, 57.72; H, 6.56; N, 10.66; S, 8.49; Cl, 8.88.

EXAMPLE 19

1-Amino-2-}2-[(5-dimethylaminomethyl-3-thienyl)methylthio]ethylamino}cyclobutene-3,4-dione A mixture of 2-[(5-dimethylaminomethyl-3-thienyl)-methylthio]ethylamine (2.11 g, 8.68 mmoles) [prepared according to the procedure described in published European patent application No. 27.744] and 1-amino-2-methoxycyclobutene-3,4-dione (1.10 g, 8.68 mmoles) in methanol was stirred at ambient temperature for 18 hours and filtered. The crude product was recrystallized from 2-methoxyethanol to yield 1.30 g of the title compound as a colorless solid, m.p. 234°–236°.

Anal. Calc'd for $C_{14}H_{19}N_3O_2S_2$: C, 51.66; H, 5.88; N, 12.91; S, 19.71. Found: C, 51.53; H, 5.64; N, 12.62; S, 19.91.

EXAMPLE 20

1-Amino-2-{2-[(5-piperidinomethyl-3-thienyl)methylthio]ethylamino}cyclobutene-3,4-dione The general procedure of Example 19 was repeated except that the 2-[(5-dimethylaminomethyl-3-thienyl)-methylthio]ethylamine utilized therein was replaced by an equimolar amount of 2-[(5-piperidinomethyl-3-thienyl)methylthio]ethylamine [prepared according to the procedure described in published European patent application No. 27,744]. The crude solid was recrystallized from 2-methoxyethanol to give the title compound (1.27 g), m.p. 236°–238°.

Anal. Calc'd for $C_{17}H_{23}N_3O_2S_2$: C, 55.86; H, 6.34; N, 11.50; S, 17.54. Found: C, 55.59; H, 6.23; N, 11.75; S, 17.62.

EXAMPLE 21

1-Amino-2-[3-(5-dimethylaminomethyl-3-thienyloxy)-propylamino]cyclobutene-3,4-dione An equimolar mixture of 4-[3-(amino)propoxy]-N,N-dimethyl-2-thiophenemethanamine [prepared according to the procedure described in published European patent application No. 27,744] and 1-amino-2-methoxycyclobutene-3,4-dione is reacted according to the general procedure of Example 19 to yield the title compound.

We claim:

1. A compound of the formula

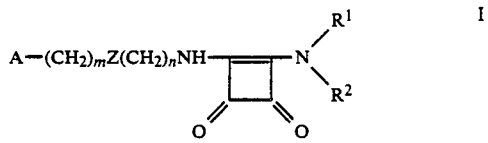

wherein $R^1$ and $R^2$ each are independently hydrogen or (lower)alkyl, and, when $R^1$ is hydrogen, $R^2$ also may be allyl, propargyl, cyclo(lower)alkyl(lower)alkyl, cyclo(lower)alkyl, cyano(lower)alkyl, 2-fluoroethyl, 2,2,2-trifluoroethyl, hydroxy, 2,3-dihydroxypropyl,

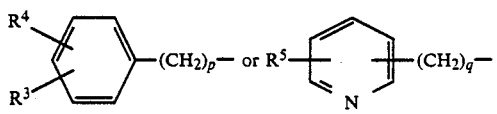

in which p is an integer of from 1 to 6 inclusive, q is an integer of from 1 to 6 inclusive, $R^3$ and $R^4$ each are independently hydrogen, (lower)alkyl, hydroxy, (lower)alkoxy or halogen, and, when $R^3$ is hydrogen, $R^4$ also may be trifluoromethyl, or $R^3$ and $R^4$, taken together, may be methylenedioxy, $R^5$ is hydrogen, (lower)alkyl, (lower)alkoxy, hydroxy, amino or halogen;

m is an integer of from 0 to 2 inclusive;

n is an integer of from 2 to 5 inclusive;

Z is sulfur, oxygen or methylene; and

A is

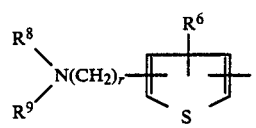

in which $R^6$ is hydrogen, (lower)alkyl, (lower)alkoxy or halogen;

r is an integer of from 1 to 4 inclusive; and $R^8$ and $R^9$ each are independently hydrogen, (lower)alkyl, allyl, propargyl, (lower)alkoxy(lower)alkyl in which the (lower)alkoxy moiety is at least two carbon atoms removed from the nitrogen atom, cyclo(lower)alkyl, or phenyl(lower)alkyl, provided that $R^8$ and $R^9$ may not both be cyclo(lower)alkyl, or $R^8$ and $R^9$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, 1,2,3,6-tetrahydropyridyl, 3-pyrrolino, momopiperidino, heptamethyleneimino, octamethyleneimino or 3-azabicyclo[3.2.2]nonane;

or a nontoxic, pharmaceutically acceptable salt, hydrate or solvate thereof.

2. A compound of claim 1 having the formula

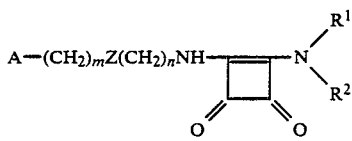

wherein $R^1$ and $R^2$ each are independently hydrogen or (lower)alkyl, and, when $R^1$ is hydrogen, $R^2$ also may be allyl, propargyl, cyclo(lower)alkyl(lower)alkyl,

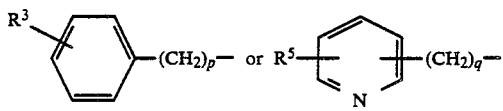

in which p and q each are independently an integer of from 1 to 6 inclusive and $R^3$ and $R^5$ each are hydrogen, (lower)alkyl or (lower)alkoxy;

m is an integer of from 0 to 2 inclusive;
n is an integer of from 2 to 5 inclusive;
Z is sulfur, oxygen or methylene; and
A is

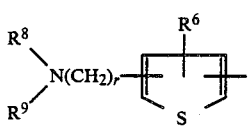

in which $R^6$ is hydrogen, (lower)alkyl or (lower)alkoxy;

r is an integer of from 1 to 4 inclusive; and $R^8$ and $R^9$ each are independently hydrogen or (lower)alkyl, or, $R^8$ and $R^9$, taken together with the nitrogen atom to which they are attached, may be pyrrolidino, methylpyrrolidino, morpholino, thiomorpholino, piperidino, methylpiperidino, N-methylpiperazino, 1,2,3,6-tetrahydropyridyl, homopiperidino, heptamethyleneimino, octamethyleneimino or 3-azabicyclo[3.2.2]nonane;

or a nontoxic, pharmaceutically acceptable salt, hydrate or solvate thereof.

3. A compound of claim 1 having the formula

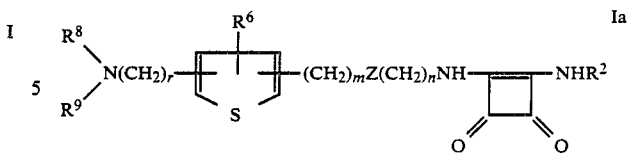

wherein $R^2$ is hydrogen, (lower)alkyl, allyl, propargyl, 3-pyridylmethyl or 6-methyl-3-pyridylmethyl;

m is an integer of from 0 to 2 inclusive;
n is an integer of from 2 to 5 inclusive;
Z is sulfur, oxygen or methylene;
$R^6$ is hydrogen or (lower)alkyl;
r is an integer of from 1 to 4 inclusive; and
$R^8$ and $R^9$ each are independently hydrogen or (lower)alkyl, or $R^8$ and $R^9$, taken together with the nitrogen atom to which they are attached, may be pyrrolidino, methylpyrrolidino, morpholino, thiomorpholino, piperidino, methylpiperidino, N-methylpiperazino, 1,2,3,6-tetrahydropyridyl, homopiperidino, heptamethyleneimino, octamethyleneimino or 3-azabicyclo[3.2.2]nonane;

or a nontoxic, pharmaceutically acceptable salt, hydrate or solvate thereof.

4. A compound of claim 3 wherein $R^2$ is hydrogen; or a nontoxic, pharmaceutically acceptable salt, hydrate or solvate thereof.

5. The compound of claim 1 which is 1-amino-2-{2-[5-dimethylaminomethyl-3-thienyl)methylthio]ethylamino}cyclobutene-3,4-dione, or a nontoxic pharmaceutically acceptable salt, hydrate or solvate thereof.

6. The compound of claim 1 which is 1-amino-2-{2-[(5-piperidinomethyl-3-thienyl)methylthio]ethylamino} cyclobutene-3,4-dione, or a nontoxic pharmaceutically acceptable salt, hydrate or solvate thereof.

7. A composition for inhibiting gastric acid secretions comprising an effective antisecretory amount of at least one compound of claim 1 and a pharmaceutically acceptable carrier.

8. A composition for treating a condition mediated through histamine $H_2$-receptors comprising at least one compound of claim 1 in an amount effective to inhibit said histamine $H_2$-receptors and a pharmaceutically acceptable carrier.

9. A method of inhibiting gastric acid secretions in an animal in need thereof comprising administering to said animal an effective antisecretory amount of at least one compound of claim 1.

10. A method of inhibiting histamine $H_2$-receptors in an animal in need thereof comprising administering to said animal an effective histamine $H_2$-receptor inhibiting amount of at least one compound of claim 1.

* * * * *